US00PP10871P

United States Patent [19]

Bradford et al.

[11] Patent Number: Plant 10,871

[45] Date of Patent: Apr. 27, 1999

[54] NECTARINE TREE NAMED 'KAY PEARL'

[76] Inventors: Lowell Glen Bradford, 12439 E. Savana Rd.; Norman G. Bradford, 11875 E. Savana Rd., both of Le Grand, Calif. 95333

[21] Appl. No.: 08/975,098

[22] Filed: Nov. 20, 1997

[51] Int. Cl.[6] ..... A01H 5/00

[52] U.S. Cl. ..... Plt./189

[58] Field of Search ..... Plt./40.1, 41.1, Plt./41.2, 189

[56] References Cited

U.S. PATENT DOCUMENTS

P.P. 7,507 4/1991 Bradford et al. ..... Plt./41
P.P. 9,959 7/1997 Bradford et al. ..... Plt./40.1

*Primary Examiner*—Howard J. Locker
*Assistant Examiner*—Ashwin Mehta

[57] ABSTRACT

The present invention relates to a nectarine tree, *Prunus persica,* and more particularly to a new and distinct variety broadly characterized by a large size, vigorous, self-fertile, productive and reqular bearing tree. The fruit matures under the ecological conditions described approximately the last week in June, with first picking on Jun. 24, 1997. The fruit is uniformly large in size, subacidic in flavor, globose in shape, freestone in type, very firm in texture, and nearly full red in skin color. The variety was a first generation cross using 'Spring Bright' (U.S. Plant Pat. No. 7,507) yellow flesh nectarine as the selected seed parent and an unnamed white flesh nectarine seedling as the selected pollen parent.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as 'Kay Pearl'. The present variety was developed by us in 1992 in a cultivated area of our experimental orchard at Bradford Farms near Le Grand, Calif. in Merced County (San Joaquin Valley). It was a first generation cross using 'Spring Bright' (U.S. Plant Pat. No. 7,507) yellow flesh nectarine as the seed parent and an unnamed white flesh nectarine seedling as the selected pollen parent. Subsequent to origination of the present variety of nectarine tree, we asexually reproduced it by budding and grafting, and such reproduction of plant and fruit characteristics were true to the original plant in all respects. The reproduction of the variety included the use of Nemaguard Rootstock, the standard of the industry in central California, upon which the present variety was compatible and true to type.

The fruit produced by the present variety is most similar to the 'Ruby Pearl' (U.S. Plant Pat. No. 9,959), by producing white flesh nectarines that mature in late June, that are subacidic in flavor, and that are full red in skin color, but is distinguished therefrom and an improvement thereon by requiring less chilling, by blooming earlier, by having a large blossom instead of small, by having globose glands instead of reniform, and by producing fruit that is larger in size and freestone instead of clingstone.

The present variety is similar to its seed parent, 'Spring Bright' (U.S. Plant Pat. No. 7,507) by producing very firm, full red nectarines that ripen the last week in June, but is very distingished therefrom by producing fruit that is white flesh instead of yellow flesh, that is freestone instead of clingstone, and that is subacidic in flavor instead of acidic.

DRAWING

The accompanying photograph exhibits four whole fruits positioned to display the characteristics of the skin color and form, one fruit divided aroung the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm eating ripe on Jun. 27, 1997. All major color code designations are by reference to the Inter-Society Color Council, National Bureau of Standards. Common color names are also used occasionally.

Tree

Size: Large, reaching 10' [3.05 meters] on third leaf trees on Nemaguard rootstock.
Vigor: Vigorous, responding typically to irrigation and fertilization.
Growth: Spreading and dense.
Form: Vase formed.
Hardiness: Hardy, able to survive typical winter weather experienced in central California.
Production: Productive, thinning necessary.
Fertility: Self-fertile.
Bearing: Regular bearer, with no alternate bearing yet observed.
Trunk:
- *Size.*—Medium, reaching 5" [127 mm.] on the third leaf on Nemaguard rootstock.
- *Texture.*—Medium rough, with roughness increasing with age.
- *Bark color.*—Grayish brown [61. gy.Br].
- *Lenticels.*—Numerous. Color: Strong Brown [55. s.Br]. Average size: ⅛" to ⅜" [3.2–9.5 mm.].

Branches:
- *Size.*—Medium, typical of the species.
- *Texture.*—Smooth on 1st year wood, increasing roughness with age.
- *Color.*—1st year wood topside: Dark red [16. d.R]. 1st year wood underside: Brilliant yellow green [116.

brill.YG]. Older wood: Moderate yellowish brown [77. m.yBr].

*Lenticels.*—Numerous, small. Color: Light orange yellow [70. L . OY]. Average size: 1/16" [1.6 mm.].

Leaves:

*Size.*—Medium. Average length: 5½" [139.7 mm.]. Average width: 1½" [38.1 mm.].

*Thickness.*—Medium.

*Form.*—Elliptical.

*Apex.*—Acuminate.

*Base.*—Acute.

*Surface.*—Smooth.

*Color.*—Dorsal Surface: Moderate olive green [125. m. OlG]. Ventral Surface: Moderate yellow green [120. m.YG].

*Margin.*—Finely serrate.

*Venation.*—Pinnately net veined.

*Petiole.*—Average length: ⅜" [9.5 mm.]. Average thickness: 1/16" [1.6 mm.]. Color: Moderate yellow green [120. m.YG].

*Stipules.*—Numerous, 2 per leaf, 2–6 per growing tip. Average length: ⅜" [9.5 mm.].

*Glands.*—Numbers: 2 to 4 per leaf. Position: Some oppositely and some alternately positioned on petiole and base of blade. Size: Medium. Form: Globose. Color: Light yellow green [119. L. YG].

Flower buds:

*Hardiness.*—Hardy, with respect to central California winters.

*Diameter.*—Typically ⅜" [9.5 mm.] 1 week before bloom.

*Length.*—Typically 11/16" [17.5 mm.] 1 week before bloom.

*Form.*—Free.

*Surface.*—Pubescent.

Flowers:

*Blooming period.*—Early as compared with other varieties.

*Onset of bloom.*—One percent on Feb. 18, 1997.

*Fragrance.*—Slight to moderate.

*Type.*—Showy.

*Average diameter.*—1¾" [44.45 mm].

*Color.*—Pale pink [7. p.Pk].

Fruit

Maturity when described: Hard ripe, Jun. 27, 1997.

Date of first picking: Jun. 24, 1997.

Date of last picking: Jul. 7, 1997.

Size: Uniform, large.

*Average diameter axially.*—2⅝" [66.7 mm.].

*Average transversely in suture plane.*—2¾" [69.9 mm.].

*Typical weight.*—6.38 ounces [181 grams].

Form: Globose, uniform.

*Longitudinal section form.*—Round.

*Transverse section through diameter.*—Round.

Suture: An inconspicuous line toward the base, becoming a shallow groove toward the apex, having a slight depression beyond the pistil point.

Ventral surface: Rounded, lipped toward the apex.

Lips: Equal.

Cavity: Flaring, rounded, elogated in suture plane with suture showing on one side.

*Depth.*—⅜" [9.5 mm.].

*Breadth.*—¾" [19.1 mm.].

Base: Rounded to slightly truncate.

Apex: Rounded.

Pistil point: Negligible in length, depressed within the suture.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—Slight in the wet season.

*Color.*—Very dark red [17. v.d.R] with strong orange yellow [68. s.OY] freckling toward the apex, with vivid purplish green [148. v.p.G] stem markings typical on some fruit.

Flesh:

*Color.*—Greenish white [153. gWhite] from skin to stone, with no bleeding and very slight moderate red [15. m.R] streaking next to the stone.

*Surface of pit cavity.*—Covered with moderate red [15. m.R] fibers.

*Amygdalin.*—Scarce.

*Juice.*—Moderate, rich.

*Texture.*—Firm, crisp.

*Fibers.*—Abundant, fine.

*Ripens.*—Even to slightly earliest at apex.

*Flavor.*—Mild subacidic and sweet, with 16 to 18 brix.

*Aroma.*—Slightly pronounced.

*Eating quality.*—Very good.

Stone

Type: Freestone.

Form: Oval.

Base: Somewhat oblique.

Apex: Acute.

Sides: Equal.

Surface: Irregularly furrowed toward the apex and pitted from the center toward the base.

Ridges: Jagged toward the base.

Color: Light brown [57. L.Br] through the wall when first removed and cracked.

Pit wall: ¼" [6.4 mm.] thick.

Tendency to split: None observed.

Kernel:

*Form.*—Oval.

*Taste.*—Bitter.

*Viable.*—Yes.

*Average width.*—½" [12.7 mm.].

*Average length.*—11/16" [17.5 mm.].

*Skin color.*—Pale yellow [89. p.Y] when first removed.

*Pellicle color.*—Moderate yellowish brown [77. m.yBr].

*Amygdalin.*—Abundant.

Use

Market: Local and long distance shipping.

Keeping quality: Fruit quality observed to remain in good condition in excess of 18 days in cold room at 36° Fahrenheit [2° Celsius].

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to the 'Ruby Pearl' (U.S. Plant Pat. No. 9,959), by producing white flesh nectarines that mature in late June, that are subacidic in flavor, and that are full red in skin color, but is distinguished therefrom and an improvement thereon by requiring less chilling, by blooming earlier, by having a large blossom instead of small, by having globose glands instead of reniform, and by producing fruit that is larger in size and freestone instead of clingstone.

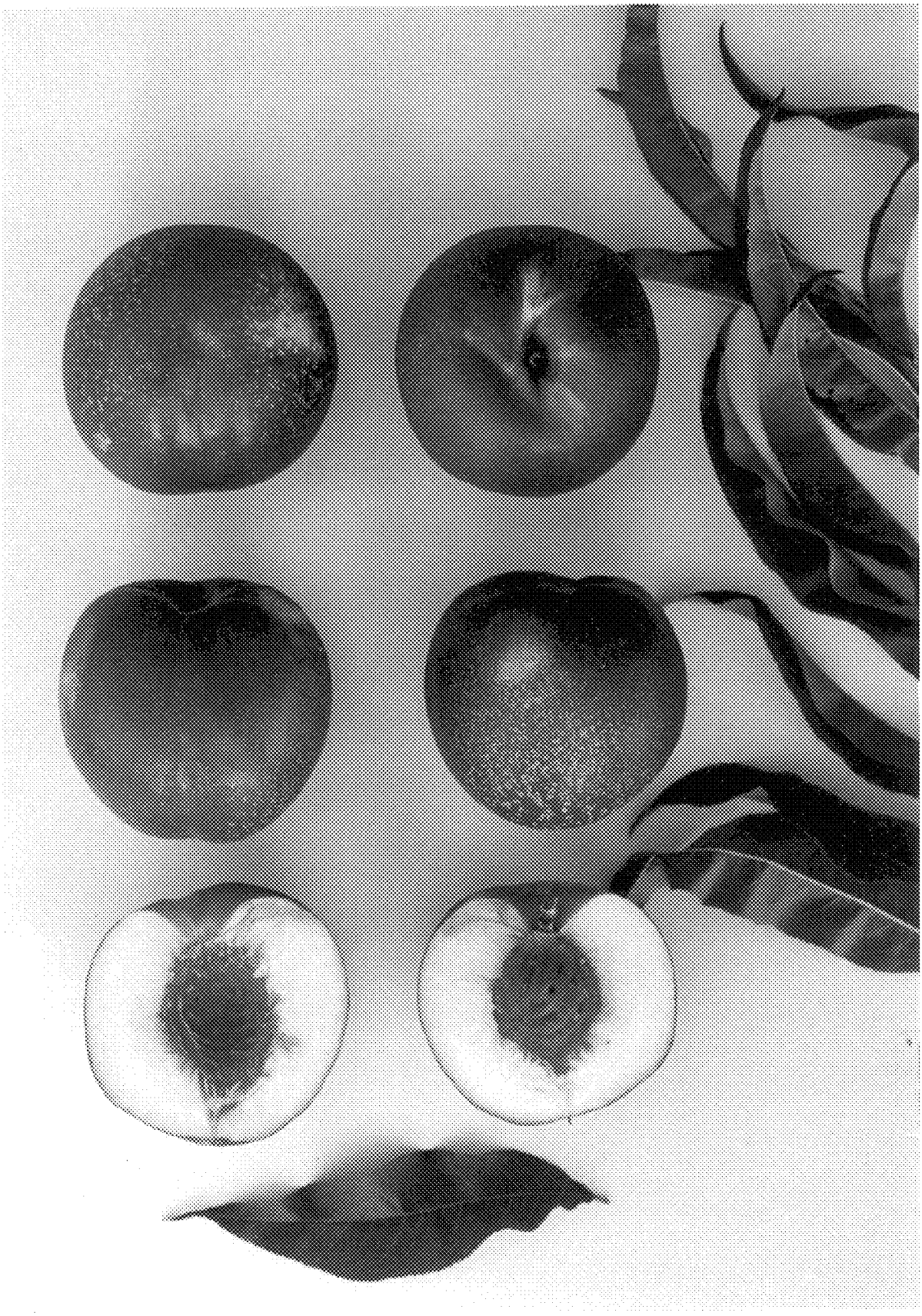

* * * * *